United States Patent
Treguer

(10) Patent No.: US 11,857,338 B2
(45) Date of Patent: Jan. 2, 2024

(54) SYSTEM FOR ANALYSING THE PHYSICO-CHEMICAL PROPERTIES OF A SKIN SURFACE

(71) Applicant: IEVA, Paris (FR)

(72) Inventor: Yann Treguer, Logonna-Daoulas (FR)

(73) Assignee: IEVA, Paris (FR)

( * ) Notice: Subject to any disclaimer, the term of this patent is extended or adjusted under 35 U.S.C. 154(b) by 908 days.

(21) Appl. No.: 16/338,077

(22) PCT Filed: Oct. 2, 2017

(86) PCT No.: PCT/EP2017/075012
§ 371 (c)(1),
(2) Date: Mar. 29, 2019

(87) PCT Pub. No.: WO2018/065380
PCT Pub. Date: Apr. 12, 2018

(65) Prior Publication Data
US 2020/0029895 A1    Jan. 30, 2020

(30) Foreign Application Priority Data
Oct. 4, 2016 (FR) ...................................... 1659545

(51) Int. Cl.
*A61B 5/00* (2006.01)

(52) U.S. Cl.
CPC .......... *A61B 5/6801* (2013.01); *A61B 5/0071* (2013.01); *A61B 5/4272* (2013.01);
(Continued)

(58) Field of Classification Search
CPC .......... A61B 2562/0219; A61B 5/1118; A61B 2562/0271; A61B 5/0022; A61B 5/02438;
(Continued)

(56) References Cited

U.S. PATENT DOCUMENTS

2004/0199058 A1   10/2004   Karam et al.
2009/0143653 A1    6/2009   Laurens et al.
(Continued)

FOREIGN PATENT DOCUMENTS

| EP | 1439782 A1 | 7/2004 |
| FR | 2603183 A1 | 3/1988 |
| JP | H10234676 A | 9/1998 |

OTHER PUBLICATIONS

Neuman, M. R. (2000, Biopotential Electrodes, J.D. Bronzino Ed., Second Edition, CRC Press LLC, Boca Raton) (Year: 2000).*
(Continued)

*Primary Examiner* — Deborah L Malamud
(74) *Attorney, Agent, or Firm* — MARSHALL, GERSTEIN & BORUN LLP

(57) ABSTRACT

The invention relates to a system for analysing physico-chemical properties of a skin surface, comprising: at least one contact sensor for applying to said skin surface to be analysed in order to determine specific information, once or twice a day, about a particular area of the skin surface; at least one environment sensor designed to accompany a user throughout the day and to measure, throughout the day, at least one external parameter acting on said skin surface; and a processing unit interfaced with the contact and environment sensors, said unit being fitted with analysis means allowing the determination of physico-chemical properties of the skin surface to be analysed, from signals generated by the contact and environment sensors.

10 Claims, 1 Drawing Sheet

(52) U.S. Cl.
CPC ............ *A61B 5/441* (2013.01); *A61B 5/4857* (2013.01); *A61B 5/4875* (2013.01); *A61B 5/7246* (2013.01); *A61B 5/7264* (2013.01); *A61B 2560/0242* (2013.01); *A61B 2562/028* (2013.01)

(58) Field of Classification Search
CPC ..... A61B 5/4836; A61B 5/486; A61B 5/4875; A61B 5/7275; A61B 5/7282; A61B 5/0002; A61B 5/0531; A61B 5/282; A61B 5/6802; A61B 5/7264; A61B 2560/0242; A61B 2560/0252; A61B 2560/0257; A61B 2562/029; A61B 5/00; A61B 10/0064; A61B 2560/04; A61B 5/0008; A61B 5/0015; A61B 5/0533; A61B 5/0537; A61B 5/103; A61B 5/14517; A61B 5/14539; A61B 5/1468; A61B 5/441; A61B 5/442; A61B 5/443; A61B 5/6801; A61B 5/6887; A61B 5/6898; A61B 5/72

See application file for complete search history.

(56) References Cited

U.S. PATENT DOCUMENTS

| | | |
|---|---|---|
| 2015/0230863 A1 | 8/2015 | Youngquist et al. |
| 2016/0058364 A1 | 3/2016 | Ionescu et al. |
| 2016/0235374 A1 | 8/2016 | Miller et al. |

OTHER PUBLICATIONS

International Search Report issued in PCT Patent Application No. PCT/EP2017/075012 dated Dec. 21, 2017.

* cited by examiner

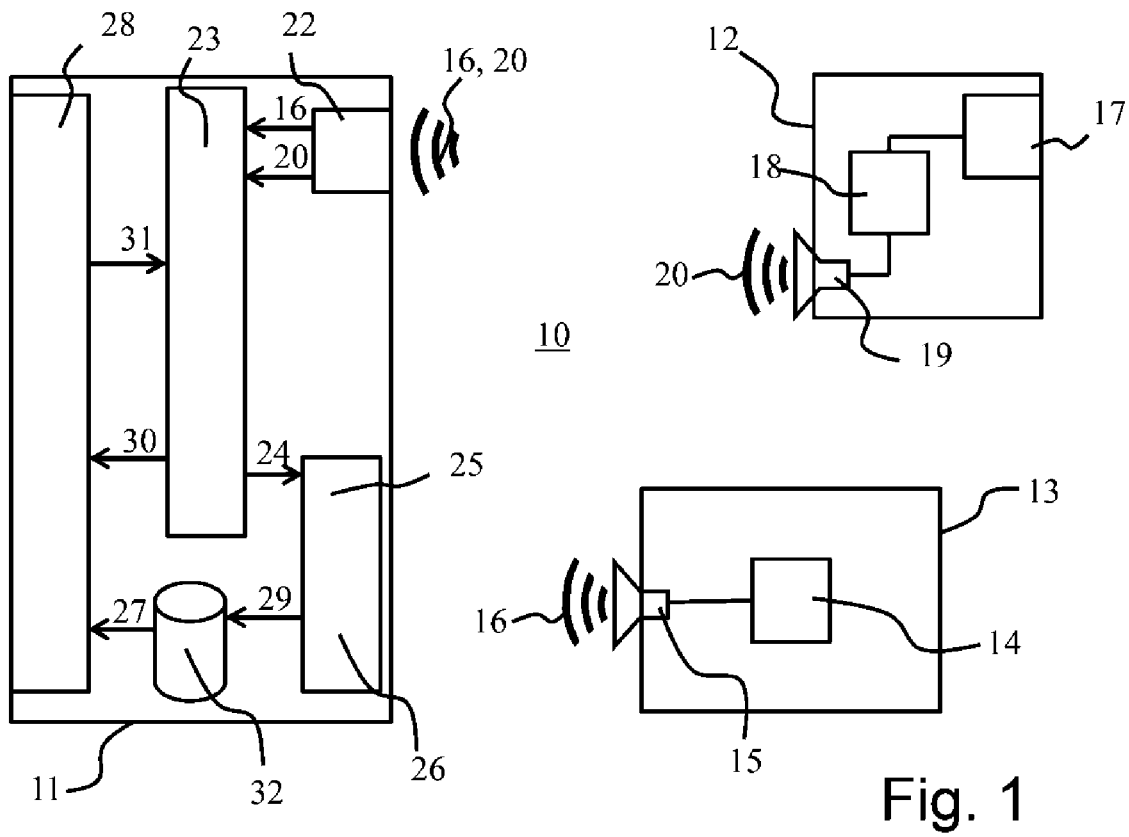
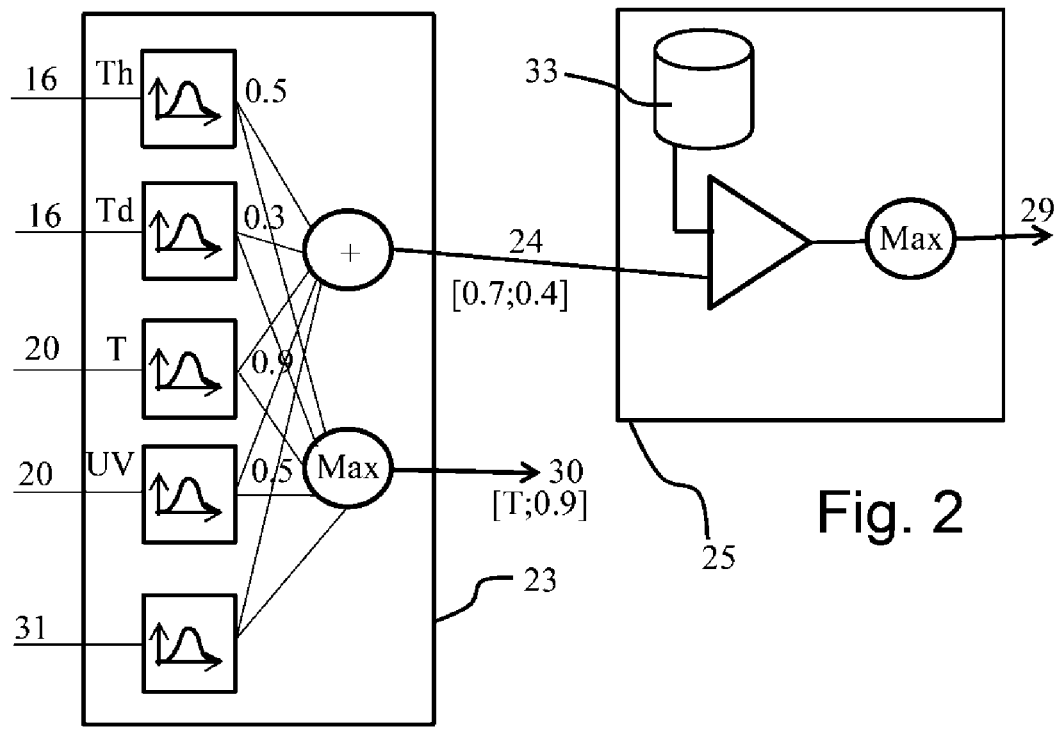

SYSTEM FOR ANALYSING THE PHYSICO-CHEMICAL PROPERTIES OF A SKIN SURFACE

TECHNICAL FIELD

The invention relates to the field of beauty including cosmetology and dermatology as well as personal care, luxury goods and life style. It relates more particularly to a system for analyzing different physico-chemical properties of a skin surface, so as to enable a recommendation to be made or to diagnose a potential treatment, and where necessary, to indicate which treatment products would be most suitable.

BACKGROUND

As is known, the skin is a major organ of the body. It enables, inter alia, control of body temperature, insulation of the internal bodily environment, limitation of water loss, protection against ultraviolet rays, while allowing the synthesis of vitamin D. It therefore plays a role of physical protection of the body, and it is the site of numerous exchanges between the body and the external environment.

This exposure to the external environment may cause degradation of its mechanical and chemical properties, as well as its visual appearance. Numerous factors, and notably atmospheric conditions, or even pollution phenomena may cause a modification of the structure of the skin and a degradation of these essential functions.

Currently, fine particles threaten the health of millions of human beings worldwide. Besides the increase in the number of cancers and pulmonary and cardiovascular diseases, these particles also have a major impact on skin aging, notably by the generation of oxidative stress.

Fine particles are particularly dangerous due to their small size combined with their large surface area per unit mass, thus making them very reactive with biological structures. Furthermore, these particles are capable of transporting chemical molecules in the mitochondria and thus of generating reactive oxygen derivatives. This is notably the case of polycyclic aromatic hydrocarbons, which are transformed into quinones, responsible for the production of reactive oxygen species. Polycyclic aromatic hydrocarbons are also capable of triggering the growth of melanocytes and therefore coloration of the skin.

A study conducted on 400 women has shown the impact of fine particle pollution on the skin. This study showed a correlation between the exposure to fine particles and signs of skin aging. Furthermore, the naso-labial fold is more pronounced in people subjected to these particles.

Besides fine particles, the external environment may also be polluted by an over-concentration of ozone, sulfur dioxide or nitrogen dioxide. Climatic conditions also have a major impact on the skin. By way of example, too much exposure to ultraviolet radiation from the sun, or to an atmosphere with too little humidity may cause a modification of the metabolism of skin cells, and for example accelerated aging. Other factors may also alter the skin, such as light, noise, cigarette smoke and exhaust fumes.

Skin dryness phenomena or the appearance of fine lines or wrinkles are thus observed. Until now, the diagnosis of a treatment intended to reduce the significance of these wrinkles is carried out by a visual examination of the skin areas to be treated. No precise quantification of the size of these wrinkles can be carried out quickly and in a widespread manner.

We know that sophisticated machines exist including devices for taking microscopic images enabling the shape and various dimensions of a wrinkle furrow to be visualized. Such machines are extremely complex, and only exist in a very limited number, which does not enable them to be used in a sufficiently widespread manner. Furthermore, such apparatus only enable the symptoms to be quantified and do not consider the causes of the latter. Simple treatment of the symptoms is not always sufficient.

Additionally, the treatment of skin dryness or of a too high lipid content is generally diagnosed by visual observation, or even a tactile examination of the skin. We can see the limitations of such an examination, as it does not enable several symptoms to be addressed simultaneously. Thus, it is recognized that different factors, such as low humidity levels of the skin and a high lipid content may interfere and lead to diagnosis errors. So, an unsuitable treatment may tend to accentuate the defects which it is seeking to rectify.

The aim of the present invention is therefore to facilitate the diagnosis of the skin treatment by objective and rigorous analysis of the physico-chemical properties of the skin.

Documents FR 2 603 183 and JP 10 234676 describe apparatus for measuring skin properties, which use specific sensors. Such apparatus have one or more different sensors which are connected by an electronic processing unit. The signals generated by these different sensors are analyzed with reference to predetermined thresholds to indicate the position of the measured values relative to the predetermined thresholds.

We believe that the analyses carried out by this type of apparatus are not actually satisfactory, since they do not take into account the influences of the various skin parameters on each other, with therefore a risk of error in diagnosis.

Furthermore, if we want to carry out the measurement of several parameters relating to a localized area of the skin, the use of several distinct sensors requires the successive positioning of the various sensors at the same place on the skin, with the risk of errors, and a significant amount of time required for the operation.

European patent EP 1 439 782 proposes to overcome this problem by the use of a device having an assembly of sensors. Although this device enables a precise and homogeneous analysis of several parameters of the skin, over a same localized area of the skin, it only enables a one-off measurement to be taken, that is to say at a precise moment, of the physico-chemical characteristics of the skin.

The invention aims to improve the quality of the estimation of the physico-chemical characteristics of the skin.

SUMMARY OF THE DISCLOSURE

The invention proposes to resolve this technical problem by using at least one environment sensor configured to accompany the user throughout the day in order to measure the conditions under which the user's skin evolves. The estimation of the physico-chemical characteristics of the skin is thus carried out by one-off measurements of the skin but also from measurements over time of at least one environment sensor.

Within the meaning of the invention, a one-off measurement corresponds to a measurement carried out manually by the user with non-predictable and variable time intervals. For example, a one-off measurement is carried out once to twice per day, in the morning and/or the evening, at variable times.

Within the meaning of the invention, a measurement over time corresponds to a measurement carried out automatically with substantially regular time intervals.

For example, a measurement over time may be carried out between 9 am and 6 pm every 10 minutes. According to another example, the time interval may vary automatically according to the difference between a current measurement and a preceding measurement. When the difference between two measurements is low, the time between two measurements may be increased, whereas when the difference between two measurements is large, the time between two measurements may be reduced.

By skin surface, we obviously imply the whole of the skin covering, including hair-covered areas, and notably the scalp.

The invention therefore relates to a system for analyzing physico-chemical properties of a skin surface, the system comprising:
- at least one contact sensor for applying to said skin surface to be analyzed in order to determine specific information, once to twice a day, relating to a particular area of the skin surface,
- at least one environment sensor configured to accompany a user throughout the day and to measure throughout the day at least one external parameter acting on said skin surface,
- a processing unit interfaced with the contact and environment sensors, said unit being fitted with analysis means allowing the determination of physico-chemical properties of the skin surface to be analyzed, from signals generated by the contact and environment sensors.

The invention thus enables the physiological parameters of the skin to be estimated by combining a one-off measurement with a measurement of the external stresses to which the skin has been subjected throughout the day. In other words, the system in accordance with the invention enables the user to simultaneously determine several pieces of information of a different nature, relating to a particular area of the skin surface and to the stresses to which this surface is subjected throughout the day.

All of this information may then be decoded so as to determine each of the physico-chemical properties of the skin surface which are of interest with a view to future treatment.

Preferably, the at least one contact sensor is configured to measure a hydration level and/or a sebum quantity and/or a desquamation level.

Preferably, the system integrates a plurality of contact sensors assembled in a restricted area, which enables representative results of the same area to be obtained for all analyzed parameters.

For example, when the contact sensor is configured to measure only a hydration level, a conventional solution consists of recommending a moisturizing cream when the hydration level measured is lower than a threshold value. The invention enables this measurement to be qualified by interpreting the conditions to which the skin has been subjected throughout the day. For example, if an external temperature measured by the environment sensor was lower than $-10°$ for several hours of the day, it is possible that the skin is dehydrated only by the contact with the cold. The invention thus enables a skin regeneration cream to be recommended rather than a moisturizing cream.

In a preferred manner, the various contact and environment sensors are made using MEMS-type technologies (Microelectromechanical System). These contact and environment sensors are thus made according to technologies using semiconducting, insulating or conducting materials, and chemical machining methods used in the field of microelectronics. The use of MEMS-type contact sensors enables all of the contact sensors to be concentrated on a particularly restricted area, implanted on a single sensor.

Preferably, the at least one environment sensor is configured to measure a temperature and/or climatic information and/or information relating to environmental pollution.

Within the meaning of the invention, a climatic information measurement corresponds to information on the air humidity level, atmospheric pressure, wind speed, quantity of ultraviolet rays received by the skin, temperature, perceived temperature (combination of temperature, humidity level and air movements), or a combination of this information.

Within the meaning of the invention, a measurement of information relating to environmental pollution corresponds to a measurement of suspended fine particles, sulfur dioxide, nitrogen dioxide, ozone, benzene, heavy metals such as lead or mercury, hydrocarbons, carbon monoxide or other volatile organic compounds, or a combination of this information.

Furthermore, information relating to environmental pollution may also concern sound pollution, which could be in the infrasound range, audible frequency range and ultrasound range, because frequencies may generate stress for the skin. For example, for the audible frequency range, a microphone, such as those integrated in a mobile phone, may be used to carry out the environment sensor function.

Furthermore, information relating to environmental pollution may also concern luminosity. Indeed, luminosity plays a biological clock regulating function via the hypothalamus. This controls the nervous system and the endocrine system which, together, regulate all biological functions of the human body. Furthermore, the hypothalamus oversees information linked to light and sends it to the pineal gland, which uses it to inform the other organs, such as the skin, about environmental light conditions.

All living things are subject to biological rhythms, that is to say biological phenomena which are repeated at regular intervals in time. The maintenance of these rhythms is essential as it constitutes one of the essential components of our well-being. The circadian rhythm, of a duration of 24 hours, enables the body to adapt to the day/night alternating periodicity. It concerns not only the awake/asleep alternation, but also other physiological parameters, such as body temperature, blood circulation, urine production, etc. When the biological clock is not in phase with major external signals, it results in malfunctioning, which leads to desynchronization of the circadian system of the body. This desynchronization is often accompanied by abnormal signs such as persistent fatigue, sleep disorders, reduced attention span, and in extreme cases depression or insomnia.

According to one embodiment, the measurement throughout time of at least one external parameter acting on said skin surface is carried out by a measurement of the position of the environment sensor coupled to information relating to climatic information determined as a function of the position of said environment sensor. This embodiment enables a server containing a plurality of environmental data to be interrogated by sending only the position of the user.

According to one embodiment, the at least one contact sensor integrates means of wirelessly communicating with said processing unit. In other words, the signals generated by the contact sensor are sent to a processing unit, with optionally initial formatting, by a Hertzian type connection. This device confers more flexibility in handling, since it is thus possible to move the contact sensor in space, over different areas of the skin of a same patient, or within the room in which the apparatus is placed, being limited only by the considerations of the range of the wireless connection. In practice, the connection may function for example according to technology known as "Bluetooth".

One could notably use the frequency band dedicated to industrial applications, also known under the abbreviation ISM Band (Industrial Scientific Medical Band) or mobile networks defined by the LTE standard covering GSM UMTS (or commonly known as 3G and 4G) standards or other telecommunications networks dedicated to connected systems.

According to one embodiment, the at least one environment sensor integrates means of wirelessly communicating with said processing unit. This embodiment enables the environment sensor to be easily transported, for example, in the form of a connected badge or watch.

According to one embodiment, the contact and environment sensors are incorporated into a same casing. This embodiment enables the user to transport the contact sensor in order to carry out a test of the skin surface at any time during the day.

According to one embodiment, the processing unit is integrated into a smartphone. This embodiment makes it possible to analyze the information received by the contact and environment sensors and to display the advice for treating the skin surface in real time as well as in nomadic use.

As a variant, the processing unit may be interfaced with a remote server which performs the analysis. To do this, the smartphone communicates the information from the contact and environment sensors securely with a server storing the user's previous information. The server then transmits to the smartphone the recommendations depending on the information received but also on the previous information.

According to one embodiment, the processing unit carries out a classification of the skin surface to be analyzed into a predetermined category according to the determined physico-chemical properties.

This classification of the skin makes it possible to associate a preventative or corrective treatment according to the skin category.

According to one embodiment, the processing unit carries out a detection of a product to be recommended according to the predetermined category and from a database of treatment products. This detection enables a particularly effective product to be suggested which will meet the needs of the skin.

BRIEF DESCRIPTION OF THE FIGURES

The way to implement the invention as well as the advantages deriving therefrom will be clearly seen from the description of the following embodiment, supported by the appended figures in which:

FIG. 1 is a schematic representation of a system for analyzing the physico-chemical properties of a skin surface according to one embodiment of the invention; and FIG. 2 is a schematic representation of the process of recommending a product to be applied to the skin according to the information received from the contact and environment sensors of the embodiment of FIG. 1.

DETAILED DESCRIPTION

The invention illustrated in FIG. 1 relates to a system 10 for analyzing physico-chemical properties of a skin surface.

The system 10 comprises a processing unit 11 associated with a contact sensor 12 and an environment sensor 13.

More precisely, the contact sensor 12 has an assembly of sensors 17 necessary for analyzing physico-chemical characteristics of the skin surface on which the contact sensor 12 is placed. Preferably, the sensors 17 implemented enable a hydration level and/or a sebum quantity and/or a desquamation level to be measured.

For example, a hydration sensor, based on MEMS technology, measures a capacitance variation between the air and the skin surface in contact with this latter. Indeed, the dielectric constant of the skin is proportional to the quantity of water that it contains. This measurement method enables the penetration of electrostatic field lines to be controlled by the geometry of the sensor (interdigital combs) and by the excitation frequency. Furthermore, this process is non-invasive and the rapidity of acquisition, less than 5 seconds, enables reactions of the skin to the contact with the sensor to be avoided.

To measure the density of sebum, two methods can be used. A first method consists in the use of the fluorescent properties of sebum. Under deep blue/near UVA radiation, sebum reacts by emitting at around 560 nm (orange-red). To do this, a monochromatic (or narrow spectral band) light source is used centered around 395 nm. The acquisition of sebum fluorescence is assured by the use of a CMOS sensor interfaced with a high-pass filter with a cut-off frequency of around 510 nm. The image obtained is segmented by image processing algorithms to quantify the surface covered by the sebum. A second method consists in the use of a patch which reacts with sebum (by becoming translucent on contact with a lipid). This patch is applied on the skin and captured by a CMOS sensor under white lighting with cross-polarization (between the emission and the CMOS sensor) obtained by using linear polarizing films. The image obtained is segmented by image processing algorithms to quantify the surface covered by the sebum.

In order to measure desquamation, it is possible to use an adhesive patch enabling dead cells to be collected by applying it to the skin. This patch is then captured by a CMOS sensor under white lighting with cross-polarization then with parallel polarization. The two images thus obtained enable the dead cells to be segmented depending on their thickness and to determine a desquamation index.

In the example of FIG. 1, the information 20 from these sensors is formatted by a component 18, for example a microcontroller, before being sent to the processing unit 11 by a wireless communication module 19.

The contact sensor 12 may take a plurality of forms without changing the invention. For example, the contact sensor 12 may be pear-shaped with a first part intended to hold the contact sensor 12 and a second part intended to place the sensors 17 in contact with the user's skin. An activation button enables a measurement to be triggered of the skin parameters of the user. As a variant, the contact sensor 12 may be connected to the processing unit 11 by a wired connection without changing the invention.

The environment sensor 13 also constitutes a nomadic object connected to the processing unit 11 by a wireless communication module 15. More precisely, the environment sensor 13 has an assembly of sensors 14 necessary for the analysis of the environment in which the user evolves throughout the day. For example, a sensor 14 may be a simple temperature sensor. Other more complex sensors 14 may also be used, such as sensors capable of detecting air quality.

For example, the company AIRPARIF® offers sensors 14 enabling fine particles to be detected. The particulate matter, or PM, is a complex mixture of extremely small particles and liquid droplets.

Particulate pollution is constituted of a number of components, including acids (for example, nitrates and sulfates), organic chemical product, metals, soil particles or dust. Particle pollution could be at the origin of 42,000 premature deaths per year in France and numerous illnesses (asthma, allergies, respiratory and cardio-vascular diseases, lung cancer).

The largest (greater than 2.5 micrometers) fall quite quickly, their duration in the air is in the order of 1 day, while the finest may remain in suspension for 1 week and travel thousands of kilometers. Once deposited, the particles may then be resuspended under the action of wind or, in an urban area, under the action of road traffic.

The size of the particles is directly linked to their potential harmfulness with regards to health. Environmental organizations are concerned by particles having a diameter less than or equal to 10 micrometers because these are the particles which generally pass through the throat and nose and penetrate into the lungs. Once inhaled, these particles may affect the heart and lungs and cause serious health effects.

The particles are classified into four categories:

PM 10, large inhalable particles such as those found near roads and industrial dusts, they are less than 10 micrometers in diameter and include fine, very fine and ultrafine particles.

PM 2.5, fine particles such as those contained in smoke and haze, are less than or equal to 2.5 micrometers in diameter. These particles may be directly emitted from sources such as forest fires, or they may form when gases, emitted by thermal power stations, industry and motor vehicles, react in the air. Diesel engines are the main source of them. Fine particles also include very fine and ultrafine particles.

PM 1, very fine particles (the most dangerous to health) are less than or equal to 1 micrometer in diameter. They are practically only eliminated by precipitation and have the time to accumulate in the air. They thus include ultrafine particles.

PM 0.1, ultrafine particles of which the diameter is less than 0.1 micrometer, also known as "nanoparticles". Their lifespan is very short, in the order of a few minutes to a few hours.

PM 2.5 and PM 1 may fall into the deepest part (alveoli) of the lungs whereupon gaseous exchanges take place between the air and blood. These are the most dangerous particles because the alveoli of the lungs have no efficient means of eliminating them and if the particles are soluble in water, they may pass into the blood stream within a few minutes. If they are insoluble in water, they remain in the alveoli of the lungs for a long period. The soluble elements may be polycyclic aromatic hydrocarbons (PAH) or benzene residues classified as carcinogenic.

The sensors 14 may consist of an optical particle detector. The operating principle of these sensors 14 is the following: when a laser beam passes through pure air, the beam is invisible. When the beam is visible, it is because the beam is diffracted on the particles throughout its path. One such particle sensor uses a near infrared source, such as an avalanche laser diode or an electroluminescent diode with a narrow emission (or beam) angle associated with an amplifier in order to detect the visibility of the beam.

Each particle which passes in front of the laser beam diffracts a part of this beam towards the sensor and, since the flow of air is constant, the width of the impulse measured enables the particles to be classified by size. A sliding average of quantities of particles per category is carried out over a period of 30 seconds.

Other types of sensors may also be used such as condensation nucleus counters, APS (Aerodynamic Particle Sizer), differential mobility analyzers, DMPS granulometers, ELPI samplers, as well as other sensors based on mass measurement detection principles.

The principle of condensation nucleus counters (CNC) is to artificially enlarge the particles by water or butanol condensation so as to be able to detect them with a conventional optical system. CNCs enable particles between 3 nm and 1.1 μm in diameter to be detected.

An Aerodynamic Particle Sizer enables the concentration of the number of particles in a particle size range of 0.5 μm to 20 μm to be provided. The principle is that of time of flight spectrometry. The sample of aerosols is accelerated into an orifice. The rate of particle acceleration is determined by their aerodynamic diameter, the largest having the lowest acceleration due to a stronger inertia. After acceleration, the particles cross a system composed of two laser beams, a mirror and a photodetector enabling them to be counted and their speed, and therefore their aerodynamic diameter, to be measured.

The Differential Mobility Analyzer (DMA) electrically charges the particles and then makes them pass into an electrostatic field, the assembly enabling the particles to exit at different times depending on their size, since the electric mobility is inversely related to the dimension of the particles. The particles are then counted using a Condensation Nucleus Counter.

The DMPS (Differential Mobility Particle Sizer) or SMPS (Scanning Mobility Particle Sizer) thus combines a DMA and a CNC. This type of apparatus enables the number of particles between 10 nm and 1 μm to be determined.

The Electrical Low Pressure Impactor (ELPI) operates using the same principle as the cascade impactors, but the particles are charged on entry into the impactor and an electrometer records the induced charges of each of the stages during the impact of the particles.

Signal analysis enables the granulometry to be characterized, within a range of 0.07 to 10 μm. An acquisition program makes it possible to visualize the distributions, by volume and by mass of the particles.

Thus, the number of sensors 14 capable of being used to implement the invention is particularly large and makes it possible to obtain very diverse information 16 about the stresses to which the skin is subjected throughout the day. The sensor 14 may also carry out a measurement of position. This measurement of position is thus transmitted to the processing unit 11 connected to a remote server making it possible to associate meteorological information or, more generally, information relating to the environment, with the position of the user.

The measurements 16 from the sensors 14 are preferably carried out regularly throughout the day while the environment sensor 13 is worn by the user. For example, the environment sensor 13 may have an internal clock which takes measurements 16 every 10 minutes.

The environment sensor 13 may take a plurality of forms without changing the invention. Preferably, the environment sensor 13 is a small object, that is to say of which the external dimensions are contained in a cube with sides of 5 cm. For example, the environment sensor 13 may be integrated into a bracelet, keyring, handbag trinket, charm or broach.

Furthermore, the contact and environment sensors 12-13 may be integrated into a single and same casing in order to limit the number of objects of the system 10.

The measurements 16, 20 from the contact and environment sensors 12-13 are thus transmitted to the processing unit 11 which integrates several bodies. Firstly, these measurements 16, 20 are received by a wireless receiver 22 which transmits these measurements to analysis means 23 enabling physico-chemical properties 24 of the skin to be determined.

An example embodiment of these analysis means 23 is illustrated in FIG. 2. Two measurements 16 from the contact sensor 12 and two measurements 20 from the environment sensor 13 are analyzed by the analysis means 23. The difference of each measurement 16, 20 is analyzed with a Gaussian function centered on the average value expected for each measurement 16, 20. The distance of the measurement 16, 20 with the Gaussian function being normalized between 0 and 1. The distances are then correlated to obtain a vector containing the physico-chemical properties 24 of the user's skin. As a variant, the Gaussian functions may be replaced by correspondence tables associating the properties of the skin with environmental parameters (as absolute value and as variation).

For example, the two measurements 20 from the contact sensor 12 may represent the hydration level Th and the desquamation rate Td of the user's skin whereas the two measurements 16 from the environment sensor may represent the temperature T and the ultraviolet rays UV to which the skin is subjected throughout the day. The distance between the hydration level Th measured and the normal level is 0.5 at the output of the first Gaussian function and the distance between the desquamation level Td of the skin and the normal level is 0.3 at the output of the second Gaussian function.

The distance between the temperature T measured over time and the temperature resistance on the hydration of the skin is 0.9 at the output of third Gaussian and the distance between the ultraviolet rays UV to which the skin is subjected and the resistance to radiation on the desquamation level is 0.5 at the output of the fourth Gaussian. It follows that the hydration level Th of the skin at the output of the analysis means 23 will be estimated as 0.7 as being the average between the distance between the hydration level Th measured and the normal level, 0.5, and the distance between the temperature T measured over time and the temperature resistance on the hydration of the skin, 0.9.

Likewise, the desquamation level Td of the skin at the output of the analysis means 23 will be estimated as 0.4. The vector containing the physico-chemical properties 24 of the user's skin at the output of the analysis means 23 will comprise the values [0.7; 0.4] according to this example.

Furthermore, the maximum of the distances from the Gaussian functions makes it possible to detect a physico-chemical property 30 of the skin having been subjected to the greatest stresses. In the previous example, the maximum of the distances is reached for the temperature T to which the skin is subjected to, which has a distance of 0.9. Thus, the most important stress factor for the skin will be estimated as being the temperature of the environment.

The vector containing the physico-chemical properties 24 of the user's skin is then transmitted to a classification body 25 of the user's skin by comparing reference vectors, stored in a database 33, with that containing the physico-chemical properties 24 of the user's skin. The maximum correlation between the reference vectors and that containing the physico-chemical properties 24 of the user's skin makes it possible to associate the user's skin with a category 29.

A treatment 27 associated with this skin category 29 is also stored in a database 32 of the processing unit 11. The processing unit 11 has a user interface 28 displaying the physico-chemical property 30 of the skin having been subjected to the greatest stresses as well as the treatment 27 proposed depending on the skin category 29 detected.

For example, if the hydration level has greatly decreased relative to a previous measurement, for example two days earlier, the processing unit 11 will precisely consider the evolution of the measurements 16 from the environment sensor. If the temperature T has greatly decreased relative to the two previous days, it is possible to conclude that the user has changed environment, for example due to a ski trip.

Thus, the drop in hydration is normal and not linked to a physiological problem. The processing unit 11 will therefore propose products having an immediate effect and not "long-term" treatment products.

According to another example of the use of environmental conditions on the physico-chemical parameters of the skin, significant variations may be noticed in the hydration levels depending on the external temperature and the relative humidity level. If the measurement of the hydration level is carried out in a one-off manner without taking into account the environmental conditions, the value obtained may appear abnormal whereas in reality it only reflects the environment.

A temperate environment, that is to say with a temperature close to 25° C. and a humidity level between 60 and 65%, enables skin to have optimal physiological functioning. The measurement of physico-chemical parameters of the skin under these conditions are thus representative of its state of health. When the relative humidity level is less than 30%, the hydration level decreases as the water loss increases to compensate for the dryness of the air. This phenomenon is amplified by extreme temperatures, that is to say temperatures below 5° C. and above 29° C.

Knowing these environmental conditions, the hydration level measured may be interpreted directly to propose a temporary suitable treatment; but this hydration level may also be corrected by the ambient temperature and the relative humidity level by using multilinear regression. The corrected hydration level is thus comparable to that measured in a temperate environment and a long-term treatment may be suggested. The determination of the multilinear regression parameters is carried out empirically by measurements on a panel of similar individuals.

Furthermore, the user interface 28 may enable the user to enter information 31, such as the type of creams applied to the user's skin during the day or medical contraindications to products. This type of information may have an impact on the classification of the user's skin and may be used by the analysis means 23.

Preferably, the processing unit 11 will be loaded onto a smartphone in order to use the processor and memory of the smartphone to carry out the processing of the measurements 16, 20. Furthermore, the processing may be partially or fully transferred to a remote server connected to the smartphone by a wireless connection.

In order to know which products 27 to use, the user initially launches the smartphone app and will be able to find information about the measurements 16, 20 from the previous days. The app may also issue information about the expected stress factors for the day, for example weather forecasts.

To carry out a one-off measurement, the user will be asked to use the contact sensor 12 and to place it on the surface to be analyzed, for example the cheekbones. The start and end of the measurement are signaled by the smartphone by a vibration if it is in silent mode or by a sound.

The app will then suggest products 27 according to this unique measurement. If the user plans to go out, the user will be asked to take the environment sensor 13 with them.

At the end of the day, the user will carry out another one-off measurement using the contact sensor 12 and the results are then correlated with the measurements 16 captured throughout the day.

The app may contain other information linked to the measurements 16, 20 carried out enabling the user to be guided in their lifestyle in order to improve the health of their skin. For example, if the user's skin is not in good health and the weather forecast predicts temperatures which are too cold for the skin, the user could be advised to limit their exposure for a few days, the time required to rebuild the epidermis.

Furthermore, the app advantageously has a configuration phase prior to using the app. This configuration phase enables user information to be acquired in order to configure the app according to the user requirements and preferences. For example, the user is invited to answer questions in this configuration phase intended to determine the brand of products preferred by the user, the average frequency of use of the products, the recurrence with which the user would like to be offered advice by the app, etc.

Also, the user may set the frequency of messages sent/displayed by the app and the user may also define thresholds above which they would always want to be alerted, for example when the fine particle pollution exceeds a predefined threshold.

The invention thus suggests particularly effective products for the user depending on two distinct measurements: a one-off measurement and a measurement performed over time in order to evaluate the stress to which the user's skin is subjected throughout the day.

The invention claimed is:

1. A system for analyzing physico-chemical properties of a skin surface, the system comprising:
   at least one contact sensor configured to be applied to said skin surface to be analyzed in order to determine a dielectric constant by measuring capacitance variation between the air and the skin surface, once or twice a day, relating to a particular area of the skin surface,
   at least one environment sensor designed to accompany a user throughout the day and to measure, throughout the day, at least one external parameter acting on said skin surface,
   a processing unit interfaced with the contact and environment sensors, said processing unit comprising a module that, responsive to receiving control signals, analyzes physico-chemical properties of the skin surface, the control signals including signals that cause:
   (i) the at least one contact sensor to take one-off measurements, wherein the one-off measurements are carried out in response to an indication from the user with non-predictable and variable time intervals,
   (ii) the at least one environment sensor to take over time measurements,
   (iii) the processing unit to receive and analyze a first signal representative of the one-off measurements and a second signal representative of the over time measurements to generate an analysis of the physico-chemical properties of the skin surface,
   (iv) the processing unit to diagnose, based on the analysis of the physico-chemical properties of the skin surface, a skin condition of the skin surface, wherein the skin condition includes at least a hydration level of the skin surface, the hydration level representative of a proportion of water on the skin surface and determined according to the dielectric constant, and
   (v) the processing unit to determine, based on the diagnosis of the skin condition of the skin surface, a suitable treatment.

2. The analysis system according to claim 1, wherein the at least one contact sensor is configured to measure the hydration level and/or a sebum quantity and/or a desquamation level.

3. The analysis system according to claim 1, wherein the at least one environment sensor is configured to measure a temperature and/or climatic information and/or information relating to environmental pollution.

4. The analysis system according to claim 1, wherein the measurement, during a period in which at least one external parameter acts on said skin surface, is carried out by a measurement of the position of the environment sensor, said external parameter being determined by climatic information as a function of the position of said environment sensor.

5. The analysis system according to claim 1, wherein the at least one contact sensor has a wireless communication module configured to communicate with said processing unit.

6. The analysis system according to claim 5, wherein the contact and environment sensors are incorporated into a same casing, and wherein the at least one environment sensor has a wireless communication module configured to communicate with said processing unit.

7. The analysis system according to claim 1, wherein the at least one environment sensor has a wireless communication module configured to communicate with said processing unit.

8. The analysis system according to claim 1, wherein the processing unit is integrated into a smartphone.

9. The analysis system according to claim 1, wherein the processing unit carries out a classification of the skin surface to be analyzed into a predetermined category according to the determined physico-chemical properties.

10. The analysis system according to claim 9, wherein the processing unit carries out a detection of a product to be recommended according to the predetermined category and from a database of treatment products.

* * * * *